United States Patent
Gramelspacher et al.

(10) Patent No.: US 10,491,604 B2
(45) Date of Patent: Nov. 26, 2019

(54) IDENTIFICATION, AUTHENTICATION, AND AUTHORIZATION METHOD IN A LABORATORY SYSTEM

(71) Applicant: Roche Diagnostics Operations, Inc., Indianapolis, IN (US)

(72) Inventors: Lothar Gramelspacher, Zurich (CH); Andrzej Knafel, Walchwil (CH); Anton Steimle, Rueti (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 241 days.

(21) Appl. No.: 14/827,790

(22) Filed: Aug. 17, 2015

(65) Prior Publication Data

US 2016/0065590 A1   Mar. 3, 2016

(30) Foreign Application Priority Data

Aug. 27, 2014 (EP) .................................... 14182373

(51) Int. Cl.
*H04L 29/06* (2006.01)
*G06F 21/33* (2013.01)
(Continued)

(52) U.S. Cl.
CPC .......... *H04L 63/123* (2013.01); *G06F 21/335* (2013.01); *G16H 10/40* (2018.01);
(Continued)

(58) Field of Classification Search
CPC . H04L 63/123; H04L 9/3234; H04L 63/0428; H04L 9/3247; H04L 63/108;
(Continued)

(56) References Cited

U.S. PATENT DOCUMENTS 7,069,444 B2 * 6/2006 Lowensohn ............ G06F 21/35
    713/185
7,552,467 B2 * 6/2009 Lindsay .................. G06F 21/31
    726/5
(Continued)

FOREIGN PATENT DOCUMENTS

| CN | 103324879 A | 9/2013 |
| CN | 103607283 A | 2/2014 |

(Continued)

OTHER PUBLICATIONS

IBM, IBM Security Access Manager for Enterprise Single Sign-On Policies Definition Guide, https://www.ibm.com/support/knowledgecenter/en/SS9JLE_8.2.0/corn.ibm.itamesso.doc/IBM_TAM_ESSO_PoliciesGuidepdf.pdf32199, retrieved Apr. 3, 2017, 163 pages.
(Continued)

*Primary Examiner* — Mohammed Waliullah
(74) *Attorney, Agent, or Firm* — Roche Diagnostics Operations, Inc.

(57) ABSTRACT

An identification, authentication and authorization method in a laboratory system is presented. The system comprises at least one laboratory device. The method comprises receiving identification data identifying a user; receiving identity confirmation data to authenticate the user; and generating authentication data upon successful authentication of the user. The authentication data is configured to enable authentication of the user based on only the identification data during a validity time period without repeated receipt of the identity confirmation data. The method further comprises receiving the identification data by an identification unit; validating the authentication data corresponding to the identification data comprising the step of verifying non-expiry of the validity time period; and granting authorization to the
(Continued)

user for the laboratory device upon successful validation of the authentication data.

22 Claims, 7 Drawing Sheets

(51) Int. Cl.
    *H04L 9/32*     (2006.01)
    *G16H 10/40*     (2018.01)
    *G06F 21/34*     (2013.01)

(52) U.S. Cl.
    CPC .......... *H04L 9/3234* (2013.01); *H04L 9/3247* (2013.01); *H04L 63/0428* (2013.01); *H04L 63/0807* (2013.01); *H04L 63/0853* (2013.01); *H04L 63/108* (2013.01); *G06F 21/34* (2013.01); *H04L 2209/24* (2013.01); *H04L 2209/72* (2013.01); *H04L 2209/805* (2013.01); *H04L 2463/082* (2013.01)

(58) Field of Classification Search
    CPC ............. H04L 63/0807; H04L 63/0853; H04L 2209/805; H04L 2209/24; H04L 2209/72; H04L 2463/082; G06F 21/335; G06F 21/34
    See application file for complete search history.

(56) References Cited

U.S. PATENT DOCUMENTS

| | | | |
|---|---|---|---|
| 7,861,929 B2 * | 1/2011 | Roth | ...................... G06Q 10/02 235/375 |
| 8,191,110 B2 | 5/2012 | Ortlam | |
| 2003/0061492 A1 | 3/2003 | Rutz et al. | |
| 2009/0069798 A1 * | 3/2009 | Muller | ................... A61B 18/12 606/33 |
| 2010/0186075 A1 * | 7/2010 | Hohlbaum | .............. G06F 21/33 726/7 |

FOREIGN PATENT DOCUMENTS

| | | |
|---|---|---|
| CN | 103856940 A | 6/2014 |
| CN | 108183907 A | 6/2018 |
| EP | 2037651 A1 | 3/2009 |
| JP | H08-30555 A | 2/1996 |
| JP | H08-50639 A | 2/1996 |
| JP | 2005-215870 A | 8/2005 |
| JP | 2005-301679 A | 10/2005 |
| JP | 2010-198062 A | 9/2010 |
| WO | 2004/044687 A2 | 5/2004 |
| WO | 2011/120450 A2 | 10/2011 |

OTHER PUBLICATIONS

Quartz Gatekeeper, Laboratory Instrument Access Control & Scheduling brochure, www.quartzimaging.com/gatekeeper-instrument-access-control-and-scheduling.html, downloaded Jul. 1, 2015, 3 pages.

Quartz Imaging, Quartz Imaging Showcases Products at M&M 2104 Meeting press release, www.prweb.com/releases/2014/07/prweb11986615.htm, downloaded Jul. 1, 2015, 1 page.

* cited by examiner

IDENTIFICATION, AUTHENTICATION, AND AUTHORIZATION METHOD IN A LABORATORY SYSTEM

CROSS-REFERENCE TO RELATED APPLICATIONS

This application claims priority to EP 14182373.2, filed Aug. 27, 2014, which is hereby incorporated by reference.

BACKGROUND

The present disclosure generally relates to an identification, authentication and authorization method and, in particular, relates to an identification, authentication and authorization method for laboratory systems and a corresponding laboratory system configured to utilize the disclosed method.

Identification and authentication techniques typically are based on one or more of three major factors: "something you know"; "something you are" and "something you have". In order to provide sufficient security, but also flexibility, authentication services of laboratory systems should be able to use different means (credential providers) for authentication like LDAP (for systems well integrated with the laboratory IT environment), identification tags (e.g., Smart Card or RFID), biometrics, or in simple systems via user ID and password.

Depending on the specific required security level, a variety of identification and authentication schemes are employed, for example:

Identification only: identification tag without identity confirmation (also known as 1-factor authentication—"what you have")

Identification and authentication: identification tag with identity confirmation (also known as 2-factor authentication—"what you have" and "what you know")

In order to comply with ever more stringent regulatory requirements related to authentication and authorization, users of laboratory systems are required to authenticate themselves for each laboratory device, for each laboratory data management system and for each laboratory information system using two-factor authentication. i.e., by identification (e.g., by an identification tag such as a radio frequency identification RFID tag) and identity confirmation (e.g., by a password or personal identification number PIN and the like). Regulatory compliance requires that users' activity at laboratory device(s) is documented in an audit trail, i.e. results production relevant action(s) are associated with the authenticated user.

In an exemplary scenario, a laboratory system comprising multiple laboratory devices (e.g., clinical lab instruments) is run during each work shift by multiple users. Each user is capable and permitted to operate at least a subset of these laboratory devices, meaning that the users may change their work places—usually many times—during a work shift. At the same time, laboratory devices of the laboratory system may enable multiple authorized users to work only during certain periods of time (e.g., work shifts).

With the currently available laboratory systems, the two-factor authentication needs to be performed multiple times per laboratory device and per working shift, all of which is highly inconvenient and results in significant productivity losses for the users. In response, quite often users of laboratory systems tend to use collective user accounts (multiple users "sharing" the same identification data and identity confirmation data) and/or fail to log out of laboratory devices between tasks and/or use other user's credentials, thereby invalidating regulatory compliance and compromising the entire security mechanism of the laboratory.

Thus there is a high demand for improving the identification, authentication and authorization workflows in laboratory systems in order to simplify the user-laboratory device interactions.

Some laboratory systems comprise non-networked laboratory devices which are not communicatively connected to other laboratory devices, data management systems and user management systems. It is however very difficult and resource-intensive to ensure regulatory compliance in laboratory systems comprising such non-networked laboratory device(s) as identification data and/or authentication data cannot be seamlessly synchronized with the rest of the systems in the laboratory.

In addition, some laboratories include one or more closed system laboratory devices that are not configurable to carry out this method without additional hardware. These closed system laboratory devices include legacy devices which lack the hardware to be configured to implement sufficient security measures (i.e., without additional hardware). Alternatively, laboratory devices which, while having the hardware resources, for some reason are not open to being reconfigured to be correspondingly (re)configured. The latter may be, for example, the case for devices from different vendors. An even further case might be when reconfiguration of existing laboratory devices is prevented by regulatory constraints. Nevertheless, closed system laboratory device(s) are often integrated into laboratory systems as their replacement with newer/other instruments is in many cases economically unjustifiable.

Therefore, there is a need to provide a secure, but at the same time convenient, identification, authentication and authorization method for a laboratory system, which can be extended to non-networked and closed system devices. In other words, there is a need to provide a solution that reduces the non-productive time users would otherwise spend for identification and authentication at laboratory devices while still maintaining high levels of security and traceability of user interactions with the laboratory devices to ensure compliance with regulatory requirements.

SUMMARY

According to the present disclosure, a laboratory system and an identification, authentication and authorization method in a laboratory system comprising at least one laboratory device is presented. The method comprises receiving identification data from an identification tag by an identification and authentication unit, the identification data identifies a user; receiving identity confirmation data by the identification and authentication unit to authenticate the user; generating authentication data corresponding to the identification data upon successful authentication of the user, the authentication data comprising a validity time period, wherein the authentication data is configured to enable authentication of the user based on the identification data during the validity time period without repeated receipt of the identity confirmation data; receiving the identification data by an identification unit from the identification tag; validating the authentication data corresponding to the identification data comprising the step of verifying non-expiry of the validity time period; and granting authorization to the user for the laboratory device upon successful validation of the authentication data.

Accordingly, it is a feature of the embodiments of the present disclosure to provide a secure, but at the same time convenient, identification, authentication and authorization method for a laboratory system, which can be extended to non-networked and closed system devices and to provide a solution that reduces the non-productive time users would otherwise spend for identification and authentication at laboratory devices while still maintaining high levels of security and traceability of user interactions with the laboratory devices to ensure compliance with regulatory requirements. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure can functionally decouple the identification process from the authentication process and can associate a validity time period (such as the duration of a work shift, for example, 8.5 hours) to a successful authentication, during which authentication of a user(s) can be enabled by identification only and without repeated input of identity confirmation data.

Generally, the disclosed identification, authentication and authorization method can be conceptually summarized by the following:

Receipt from a user and validation of identification data and identity confirmation data;

Generation of authentication data comprising a validity time period of the same;

Authorization of the user for a laboratory device during the validity time period by receipt of only identification data from the user, the authorization being based on validation of authentication data corresponding to the user-provided identification data.

Embodiments of the disclosed method and system can combine the security of a two-factor authentication (identification and identity confirmation) with the convenience of one-factor authentication (identification only).

Accordingly, in certain embodiments, the identification, authentication and authorization method comprises:

receiving identification data from an identification tag by an identification and authentication unit, the identification data identifying a user;

receiving identity confirmation data by the identification and authentication unit to authenticate the user;

generating authentication data corresponding to the identification data upon successful authentication of the user, the authentication data comprising a validity time period, wherein the authentication data is configured to enable authentication of the user based on the identification data during the validity time period without repeated receipt of the identity confirmation data, the authentication data being associated with the identification data;

receiving the identification data by an identification unit from the identification tag;

validating the authentication data corresponding to the identification data comprising the step of verifying non-expiry of the validity time period;

granting authorization to the user for the laboratory device upon successful validation of the authentication data.

Further embodiments of providing a user identification, authentication and authorization method accommodating non-networked laboratory devices (i.e., not communicatively connected to the laboratory system) can be met in by the authentication data (comprising its validity time period) being stored on the identification tag itself, such as to be later retrievable by an identification unit of a non-networked laboratory device(s), thereby enabling a secure but convenient authentication of the user during the validity time period. The identification data can be provided by the user (e.g., in the form of a tag), without the need for repeated identity confirmation data and authentication based on validation of authentication data retrieved from the identification tag. In other words, the identification tag can act as a temporary storage (possibly encrypted and/or digitally signed) of authentication data, the identification tag can be the information carrier "substituting" the lacking communicative connection of the non-networked laboratory device.

Certain embodiments of the disclosed identification, authentication and authorization method can accommodate securing of closed system laboratory device(s) (i.e., with no integrated processing unit configurable to decouple identification from authentication, (e.g., according to the disclosed method or a disclosed system) and is addressed according to these certain embodiment(s) in that the identity confirmation data can be stored within the authentication data upon successful authentication of the user and in that a credential cache device can be connected between a human interface device and a credential input interface of the closed system laboratory device. This credential cache device can authenticate the user for the closed system laboratory device by transmitting the identification data and the identity confirmation data to the credential input interface (e.g., by replicating keystrokes of a keyboard) of the closed system laboratory device upon identifying the user.

The term "laboratory device" as used herein can refer to any kind of automated; semi-automated or manual device for use in laboratory work in the clinical, chemical, biological, immunology or pharmaceutical area or the like. Such a laboratory device may comprise, amongst other things, at least one of an analytical instrument (such as clinical chemistry analyzers, coagulation chemistry analyzers, immunochemistry analyzers, urine analyzers), a transfer device (such as a conveyor, gripper, magnetic transfer surface), a storage unit, a liquid processing unit (such as a pipetting unit), a processor (such as a sample preparation device), a user interface, a mixing unit (such as a stirrer; a shaker or an agitator), a tempering device (such as a heater/cooler), a waste station, an aliquoter, a data management system, laboratory information system LIS or the like.

The term "non-networked laboratory device" as used herein can refer to any laboratory device which is not connected to a laboratory network that can allow the laboratory device to access previously stored authentication data over a network. It shall be noted however, that other types of network connections (i.e., for any purpose/capability other than accessing authentication data) may or may not be provided for in such "non-networked laboratory device." Therefore, the term "non-networked" can be interpreted in a limited sense to the lack of this purpose-specific network connection.

The term "closed system laboratory device" as used herein can refer to any laboratory device as hereinbefore defined which are not configurable to carry out the disclosed method by themselves (i.e., without additional hardware and/or software). These closed system laboratory devices can include legacy devices which lack the hardware to be configured to implement identification and authentication functions, such as the disclosed method or alternatively laboratory devices which while having the hardware resources, for some reason cannot be reconfigured to be correspondingly (re)configured. The latter may be for example the case for devices from different vendors. An even further case might be when reconfiguration of existing laboratory devices is prevented by regulatory constraints. Therefore, the term "closed system" can be interpreted in a limited sense as to mean a lack of configurability for this precise function. The term may not be interpreted that such devices cannot be configurable for any reason.

The term "laboratory system" may be used herein to refer to any system comprising one or more laboratory device(s).

The term "user" as used herein can be a human who may be represented and identified by identification data, for example a user-ID (UID), i.e., a unique sequence of characters particular to a user and used to identify the user at one or more laboratory devices and corresponding authentication. In particular, the user-ID may be a secret character sequence comprising alphanumeric or special characters or a mixture thereof.

The term "identification tag" as used herein can refer to any form of identifier suitable to uniquely identify a user, such as a barcode or a radio frequency identification (RFID) tag.

The term "RFID tag" as used herein can refer to either an active or passive RFID tag that contains information. An RFID tag or transponder can include a coil or antenna and some information stored on an RFID chip that can be read and/or written by an RFID reader. Correspondingly, the RFID tag can be read only or read/write and the information associated with the RFID tag can be hard-coded into the RFID tag at the time of manufacture or at some later time. The information stored on an RFID tag can include at least a unique identifier UID.

The term "RFID reader" as used herein can include devices that can read information from and/or write information into an RFID tag. RFID readers can comprise or can be connected to a reader antenna and circuitry to transmit and receive signals with the antenna. The RFID reader antenna can generate an electromagnetic field, thereby transferring energy to the tag. Depending on the design of the tag, a portion of the energy transferred to the tag can be reflected to the reader so as to provide information about the tag back to the reader.

In some countries, there can be regulatory health requirements which do not allow wearing bracelets as RFID tags below the elbow during laboratory work, according to various embodiments the RFID tag—as an embodiment of the identification tag—may take up one of the following physical forms:

1. a card (badge attached to the clothes or on a leash);
2. a band (bracelet, headband, ankle band, and the like);
3. a work protective glass;
4. a key fob;

5. clothes with embedded/weaved-in RFID transponder (e.g., gloves, sleeve, shoes);
6. a sticker attached to clothes or to personal artifacts;
7. a personal artifact with embedded transponder (e.g., pen/pencil, cigarette lighter, purse, wallet, glasses (personal optical glasses);
8. a bijouterie (finger-ring, earring, toe-ring, and the like); or
9. a body part embedded or attached transponder (e.g., piercing).

Correspondingly the reader antenna of the RFID reader—as an embodiment of the identification tag reader—can be embedded with the RFID reader/writer/controller or attached by cable and be in the form of:
1. embedded in the laboratory device;
2. item attached to the laboratory device (e.g., near a display)
3. item located on the desks of a laboratory table (e.g., small box with embedded reader/writer, controller and antenna);
4. item attached to a piece of furniture;
5. floor mat/carpet;
6. seat or chair-cover; or
7. loop near/through which a body part needs to pass to gain access to the working area, (e.g., a frame around a touch screen monitor).

The term "identification" can be used herein to refer to the first factor of two-factor authentication, i.e., the act of identifying a user of the laboratory system based on something the user possesses. The identification can be based on the identification data.

The identification data may be entered by the user via a human interface device such as a keyboard, a touch-screen, a biometric reader (such as a fingerprint reader, a retina scanner or a face recognition device) and/or a mouse in combination with a credential input interface. Alternatively, the identification data may be stored on the identification tag.

The term "identity confirmation" can be used herein to refer to the second act of two-factor authentication, i.e., confirming the user's identity based on something the user knows, namely identity confirmation data such as a password, a personal identification number (PIN) or the like.

The term "authentication" can be used herein to refer to the act of authenticating the user (at least two-factor authentication) comprising:
identification of the user; and
validation of correctness of the identity confirmation data against a record of registered users of the laboratory system.

Correspondingly, the term successful authentication of the user can refer to successful identification of the user and successful validation of the corresponding identity confirmation data.

The term "authentication data" as used herein can refer to data related to the authentication of the user, including but not limited to identification data; data related to access authorization(s) of the user to individual laboratory device(s) and/or group(s) of laboratory devices. The authentication data can further comprise a validity time period, i.e., a period of time during which the authentication data of the particular user is valid.

The term "enable authentication" with respect to the authentication data being configured to enable authentication of the user (based on only the identification data during the validity time period without repeated receipt of the identity confirmation data) can be used here such that the authentication data can be configured such as to comprise all data (such as, for example, general authorization data, device class/group specific authorization data and/or device instance specific authorization data) necessary for the authentication of the user with a laboratory device. In other words, "authentication data configured to enable authentication of the user" can mean authentication of the user can be possible without any additional data.

The term "human interface device" as used herein can refer to any kind of device for a user to interact with any component of a laboratory device, such as but not limited to keyboards, mice, alphanumeric keypads, touchscreen display devices, and the like. The identification tag reader may not be referred to as belonging to the group of human interface devices.

The term "credential input interface" as used herein can refer to any kind of interface configured such as to facilitate provision of identification data and/or identity confirmation data.

Figure 1:
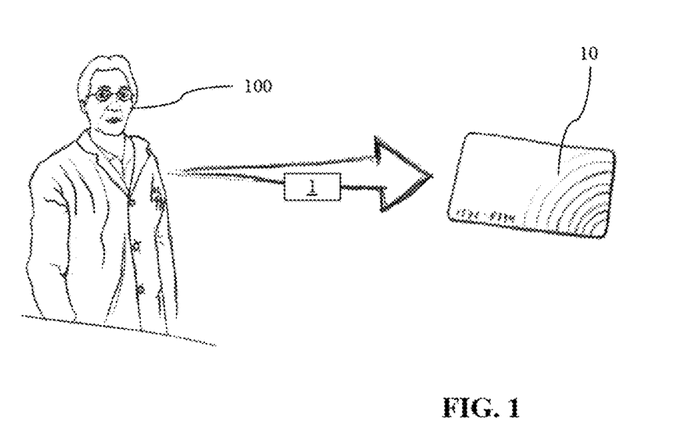
FIG. 1 illustrates a schematic diagram illustrating a user and an identification tag storing identification data associated with the user according to an embodiment of the present disclosure.

As depicted on the schematic diagram of FIG. 1, a user 100 is identified by identification data 1 stored on an identification tag 10. According to one embodiment, the identification tag 10 can be a RFID tag.

Figure 2:
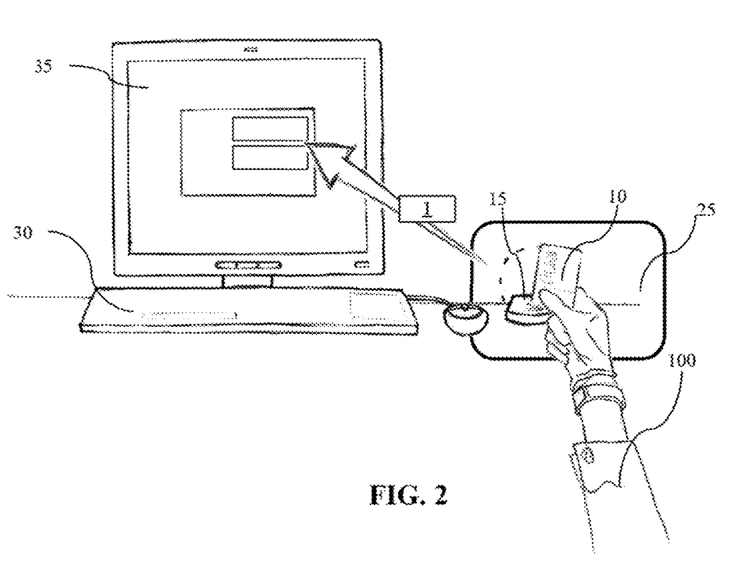
FIG. 2 illustrates a schematic diagram illustrating receipt of identification data from an identification tag by an identification and authentication unit according to an embodiment of the present disclosure.

FIG. 2 depicts a schematic diagram illustrating receipt of identification data 1 from an identification tag 10 by an identification and authentication unit 25. As illustrated on FIG. 2, according to one embodiment, the identification data 1 can be provided to the identification and authentication unit 25 by causing the identification data 1 to be transmitted from the identification tag 10 to an identification tag reader 15. In exemplary embodiments, the identification tag reader 15 can be a RFID reader.

Alternatively, the identification data 1 may be provided to the identification and authentication unit 25 by a human interface device 30, such as a keyboard for example, operatively connected to the identification and authentication unit 25, in such embodiments, the identification data 1 can be provided via a credential input interface 35.

According to other embodiments, the identification and authentication unit 25 can be a stand-alone device of the laboratory system 300 or functionally and/or structurally integrated into one or more laboratory device(s) 200.

Figure 3:
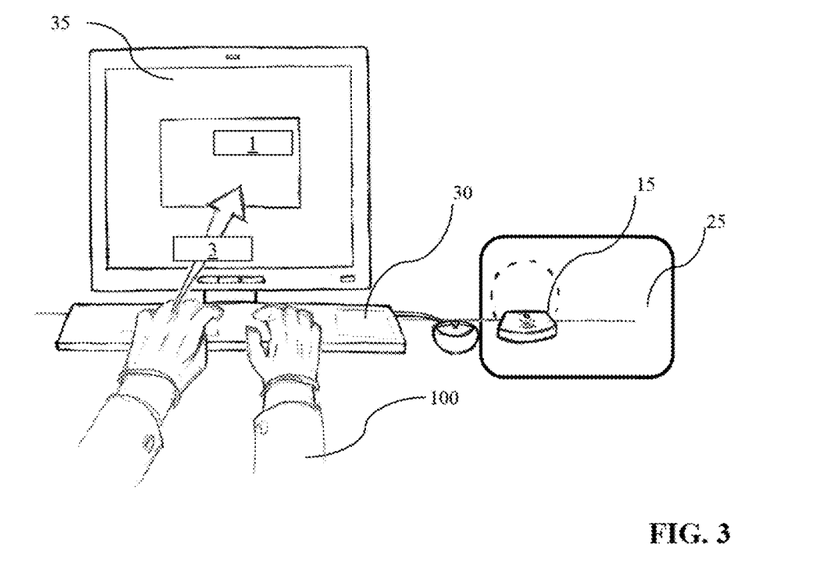
FIG. 3 illustrates a schematic diagram illustrating receipt of identity confirmation data by the identification and authentication unit to authenticate the user according to an embodiment of the present disclosure.

FIG. 3 illustrates the next step of the disclosed method, namely the receipt of identity confirmation data 3 by the identification and authentication unit 25 to authenticate the user 100. According to one embodiment, the identity confirmation data 3 can be provided by the user 100 by the human interface device 30, such as a keyboard, operatively connected to the identification and authentication unit 25. The identity confirmation data 3 can comprise (but is not limited to) one or more of the following: a password, PIN, and the like.

After receipt of the identification data 1 and identity confirmation data 3, the identification and authentication unit 25 can attempt to authenticate the user 100 with the laboratory system 300. The authentication of the user 100 can comprise a validation of the correctness of the identity confirmation data 3 against a record of registered users of the laboratory system 300. According to one embodiment, the authentication may also comprise the steps of verifying access authorization(s) of the user 100 to individual laboratory device(s) 200 and/or group(s) of laboratory devices 200. When identification of the user 100 and validation of the corresponding identity confirmation data 3 are both successful, the user 100 can be authenticated.

Figure 4:
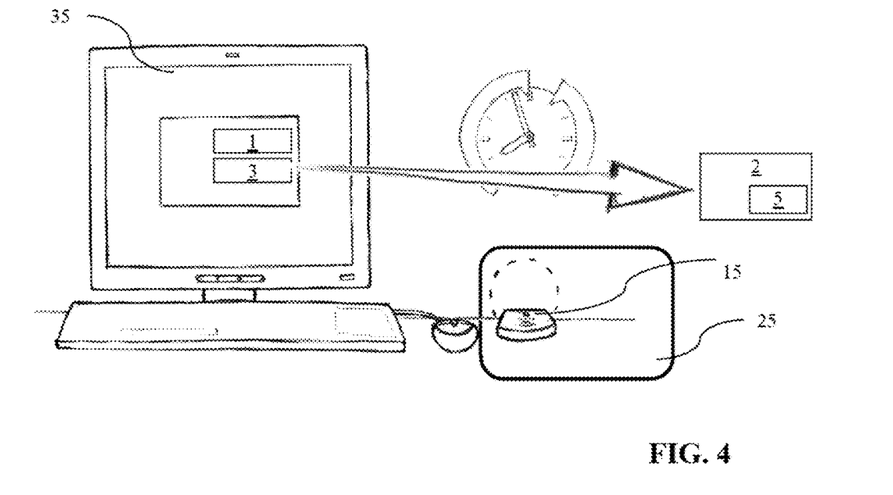
FIG. 4 illustrates a schematic diagram illustrating generation of authentication data corresponding to the identification data upon successful authentication of the user, the authentication data comprising a validity time period according to an embodiment of the present disclosure.

The step of generation of authentication data 2 corresponding to the identification data 1 upon successful authentication of the user 100 is illustrated on FIG. 4. As illustrated by a clock face, the authentication data 2 can be provided with a validity time period 5, i.e., a period of time during which the authentication data 2 of the particular user 100 may be valid, the authentication data 2 enabling authentication of the user 100 based only on the identification data 1 during the validity time period 5 without repeated receipt of the identity confirmation data 3. Upon its generation, the authentication data 2 can be associated with the corresponding identification data 1.

In some embodiments, the authentication data 2 can be generated in the form of a so-called authentication token with a validity time period 5. For example, the authentication data 2, comprising the entire information required to authenticate the user 100 with a laboratory device 200, may have a content/format as in the example table 1 shown below:

TABLE 1 example of authentication data 2 content and format.

| Authentication Data | Encryption | Signature |
|---|---|---|
| User Identification/Authentication/ Authorization Token | Encryption using the | Digital signature |
| User Identity | | |
| General authorization | RFID | |
| User Roles | transponder | |
| Access Attributes | technology | |
| Device Class specific authorization (e.g., based on user training) | | |
| Device Class ID | | |
| User Roles | | |
| Access Attributes | | |
| Device Instance specific authorization | | |
| Device Instance ID | | |
| User Roles | | |
| Access Attributes | | |
| User Identification/Authentication Credentials | | None |
| Device Instance specific credentials | | |
| Device Instance ID | | |
| User-name | | |
| Password | | |
| Token Validity | | None |
| Validity Time Period | | |

Figure 5:
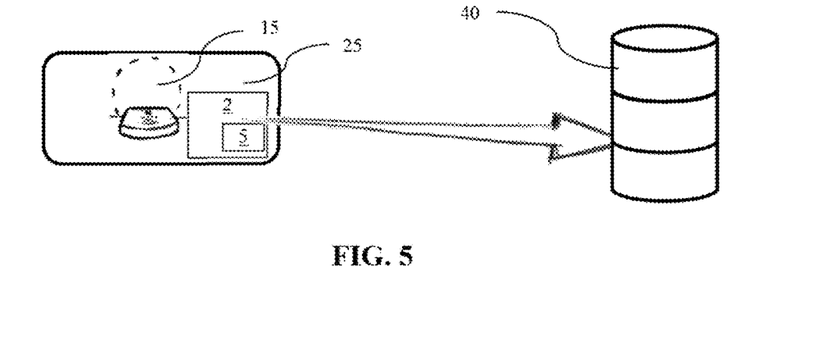
FIG. 5 illustrates a schematic diagram illustrating storing the authentication data by the identification and authentication unit in an authentication data repository according to an embodiment of the present disclosure.

The schematic diagram of FIG. 5 illustrates an embodiment wherein the authentication data 2 can be stored by the identification and authentication unit 25 in an authentication data repository 40. This authentication data repository 40 can be accessible by the identification unit 27 directly and/or by a network connection. According to one embodiment, the authentication data 2 can be encrypted and/or digitally signed before being stored by, for example, using a preconfigured private encryption key.

Figure 6:
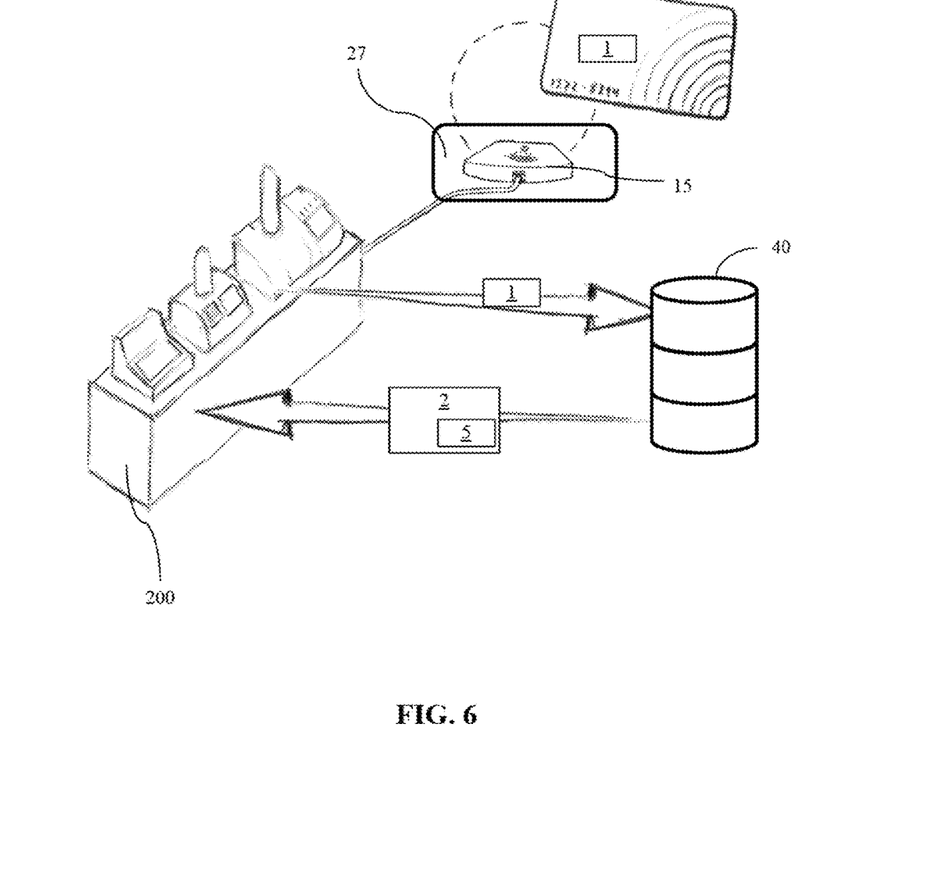
FIG. 6 illustrates a schematic diagram illustrating receipt of identification data by an identification unit connected to a laboratory device from the identification tag and retrieval of authentication data corresponding to the identification data according to an embodiment of the present disclosure.

FIG. 6 illustrates the process of (repeated) authentication of a user 100 with a laboratory device 200 of the laboratory system 300 after initial authentication (by identification and identity confirmation) with the identification and authentication unit 25. It can be noted that the (repeated) authentication can be at the same or a different laboratory device 200 than the laboratory device 200 of initial authentication.

In a first step of the (repeated) authentication of a user 100 with a laboratory device 200, identification data 1 can be received from the identification tag 10 by an identification unit 27. According to some embodiments, the identification data 1 can be received from the identification tag 10 by the identification unit 27 by causing the identification data 1 to be transmitted from the identification tag 10 to an identification tag reader 15 operatively connected to the identification unit 27.

In a second step, the authentication data 2 corresponding to the identification data 1 can be validated. In the embodiment illustrated in FIG. 6, the authentication data 2 can be retrieved from the authentication data repository 40 where it has been previously stored. Alternatively, the identification unit 27 may be operatively connected with the identification and authentication unit 25 such as to make the authentication data 2 generated by the identification and authentication unit 25 available to the identification unit 27. In an additional embodiment, the identification and authentication unit 25 functionally and/or structurally can comprise the identification unit 27.

According to some embodiments where authentication data 2 was encoded, the identification unit 27 can be configured to decrypt the authentication data 2 after retrieving it, for example, using a preconfigured public key corresponding to the private key of the identification and authentication unit 25.

The validation of the authentication data 2 corresponding to the identification data 1 can comprise at least the step of verifying non-expiry of the validity time period 5. According to another embodiment, the validation of the authentication data 2 may also comprise the step of verifying access authorization(s) of the user 100 to a particular laboratory device(s) 200 and/or group(s) of laboratory devices 200 for a selective authorization of the user 100.

Upon successful validation of the authentication data 2, authorization can be granted to the user 100 for the laboratory device 200. The authorization can comprise but not limited to one or more of the following:
right to access data on the laboratory device 200;
right to perform clinical, chemical, biological, immunology or pharmaceutical procedures such as sample analysis with the laboratory device 200;
right to configure the laboratory device 200;
right to perform maintenance work on the laboratory device 200.

Figure 7:
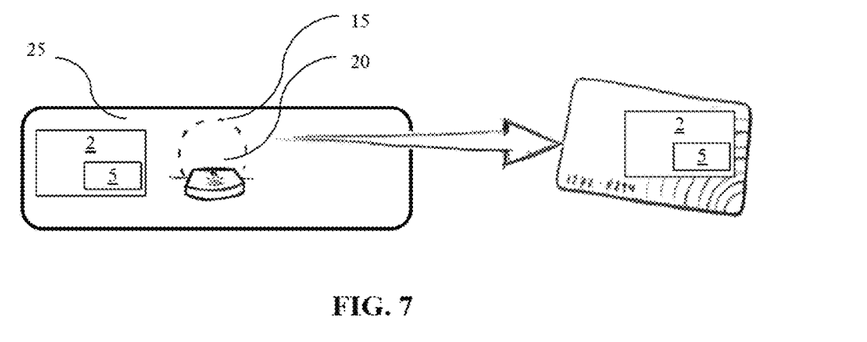
FIG. 7 illustrates a schematic diagram illustrating storage of the authentication data on the identification tag in an embodiment of the invention extended to non-networked laboratory devices according to an embodiment of the present disclosure.
Figure 8:
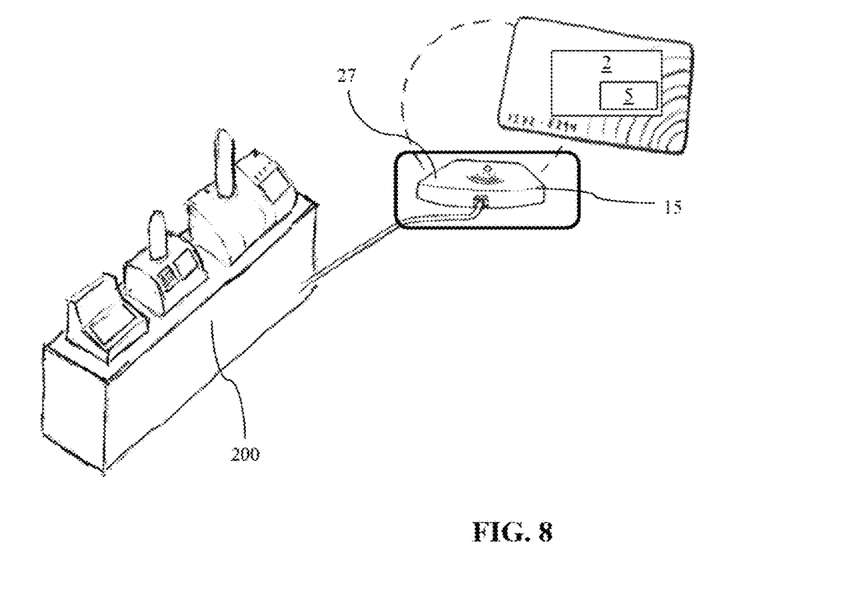
FIG. 8 illustrates a schematic diagram illustrating retrieval of authentication data from the identification tag by an identification unit connected to a non-networked laboratory device according to an embodiment of the present disclosure.

FIGS. 7 and 8 illustrate some embodiments wherein the identification tag 10 can act as (temporary) storage and transport medium for the authentication data 2. Using the identification tag 10 as a (temporary) storage and transport medium for the authentication data 2 can be particularly advantageous in the case the laboratory system 300 can comprise at least one non-networked laboratory device 200 which is not communicatively connected as to access the authentication data 2, neither from a authentication data repository 40 where it has been previously stored nor from the identification and authentication unit 25 where it has been generated.

FIG. 7 shows a schematic diagram illustrating storage of the authentication data 2 on the identification tag 10 by an identification tag writer 20, wherein the identification tag 10 can be a writable identification tag 10.

FIG. 8 shows a schematic diagram illustrating the retrieval of authentication data 2 from the identification tag 10 by an identification unit 27 connected to a laboratory device 200. It can be understood that after retrieval of the authentication data 2, the further steps of validation and authorization can, at least conceptually, be identically performed as according to embodiments described above with reference to FIG. 6. In this way the secure, but at the same time convenient, identification, authentication and authorization method can be extended to non-networked devices.

FIGS. 9-13 illustrate some embodiments wherein a credential cache device 50 can be used to accommodate closed system laboratory devices that may not be configurable to carry out the embodiments of the method hereinbefore described without additional hardware.

Figure 9:
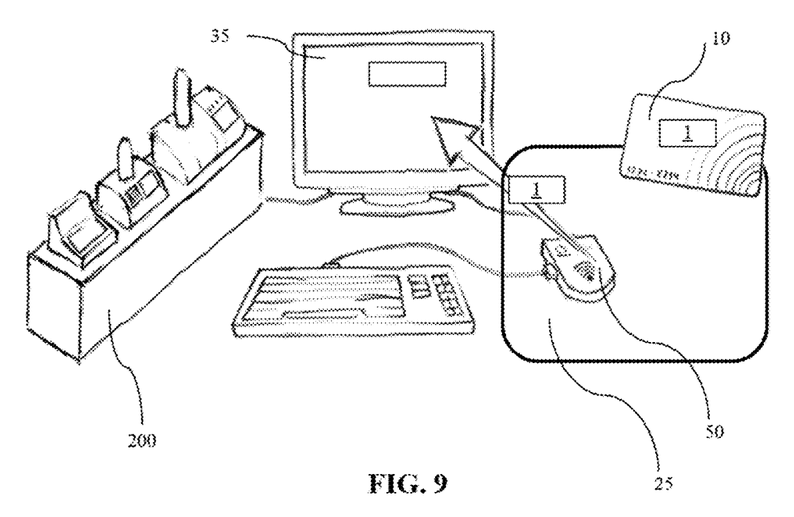
FIG. 9 illustrates a schematic diagram illustrating a credential cache device connected between a human interface device and a credential input interface of a closed system laboratory device and receipt of identification data by the credential cache device from an identification tag according to an embodiment of the present disclosure.

FIG. 9 illustrates connection of a credential cache device 50 between, functionally and/or structurally, a human interface device 30 and a credential input interface 35 of a laboratory device 200. According to one embodiment, identification data 1 can be received by the credential cache device 50 from an identification tag 10 and can then be forwarded to the credential input interface 35 of a laboratory device 200. Alternatively, the identification data 1 can be manually inputted by the user 100 via the human interface device 30.

Figure 10:
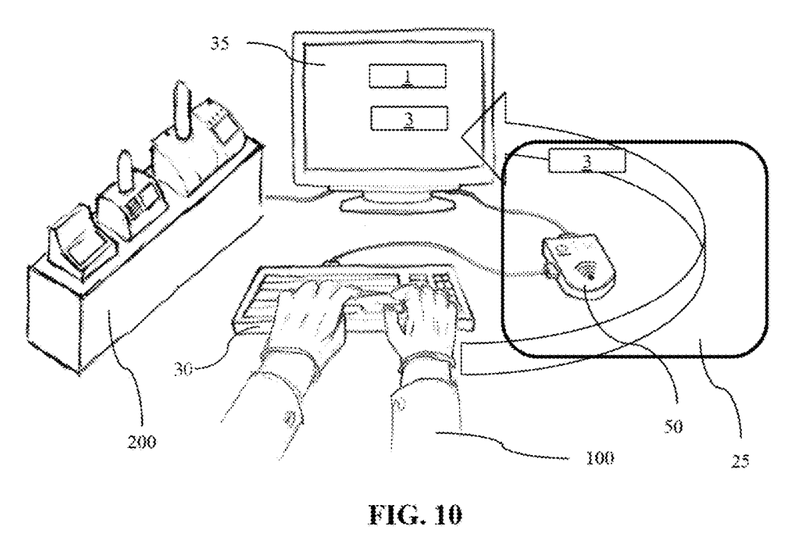
FIG. 10 illustrates a schematic diagram illustrating recording of the identity confirmation data by the credential cache device according to an embodiment of the present disclosure.

FIG. 10 shows the step of recording of the identity confirmation data (ICC) by the credential cache device 50 as it can be provided by the user 100 via the human interface device 30.

Figure 11:
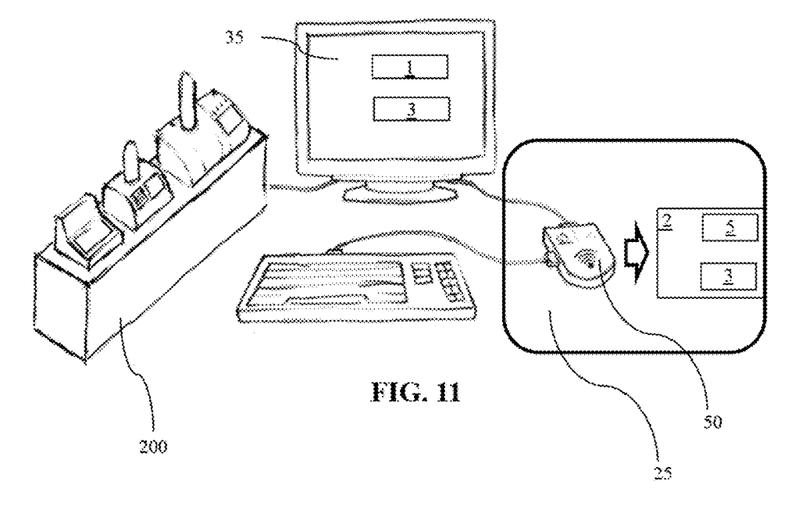
FIG. 11 illustrates a schematic diagram illustrating storage of the identity confirmation data within the authentication data according to an embodiment of the present disclosure.

FIG. 11 illustrates the storage of the ICC within the authentication data 2, as needed so that the credential storage device 50 can provide it later to the credential input interface 35 for repeated authentication of the user 100 within the validity time period 5.

According to some embodiments, the credential cache device 50 can comprise and/or can be operatively connected to the identification and authentication unit 25.

Figure 12:
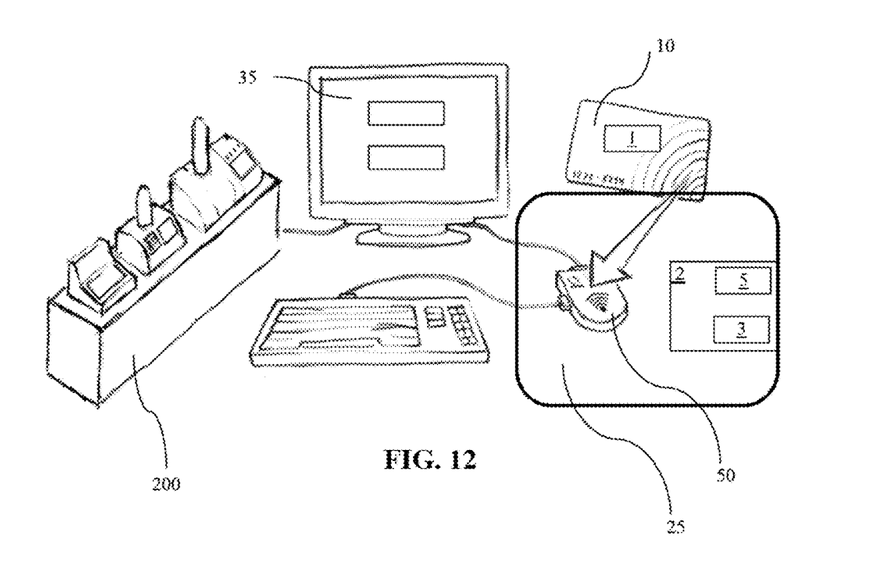
FIG. 12 illustrates a schematic diagram illustrating receipt of identification data by the credential cache device according to an embodiment of the present disclosure.

FIG. 12 shows receipt of identification data 1 by the credential cache device 50 from the identification tag 10 and retrieval of the corresponding authentication data 2, including the identity confirmation data 3. According to some embodiments, the credential cache device 50 can be communicatively connected to the identification and authentication unit 25 and/or to an authentication data repository 40 such as to make the authentication data 2 available thereto. Alternatively, the authentication data 2 may be stored on the identification tag 10 to be later retrieved therefrom by the credential cache device 50, the latter comprising an identification tag reader 15.

Figure 13:
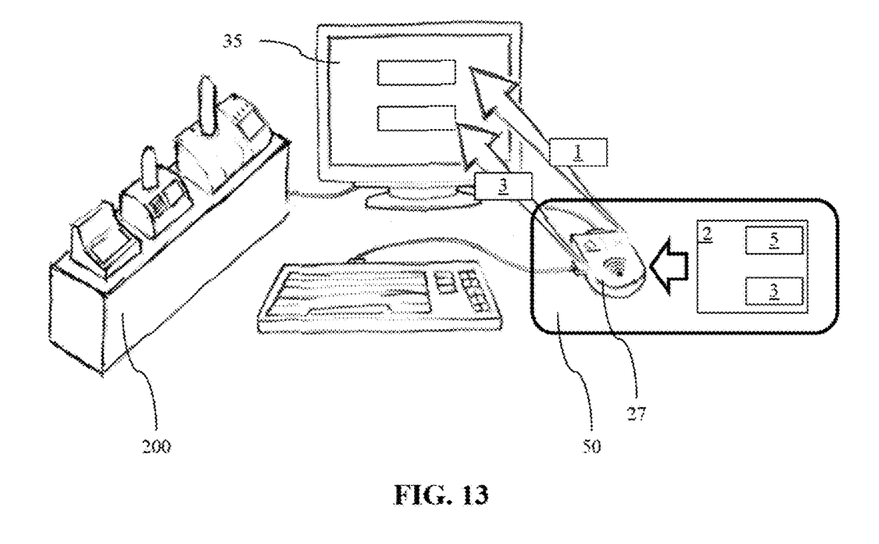
FIG. 13 illustrates a schematic diagram illustrating the credential cache device transmitting the identification data and the identity confirmation data to the credential input interface of the closed system laboratory device according to an embodiment of the present disclosure.

FIG. 13 illustrates the credential cache device 50 transmitting the identification data 1 and the identity confirmation data 3 to the credential input interface 35 of the laboratory device 200. According to some embodiments, the credential cache device 50 can emulate the keystrokes of a keyboard to provide the identification data 1 and the identity confirmation data 3 to the credential input interface 35, the use of the credential cache device 50 can be transparent to the laboratory device 200. The authentication and authorization of the user 100 can be performed by the laboratory device 200 just like it can be if the user 100 had provided the credentials manually using a keyboard. In this way the secure, but at the same time convenient, identification, authentication and authorization method can be extended to closed system devices.

Figure 14:
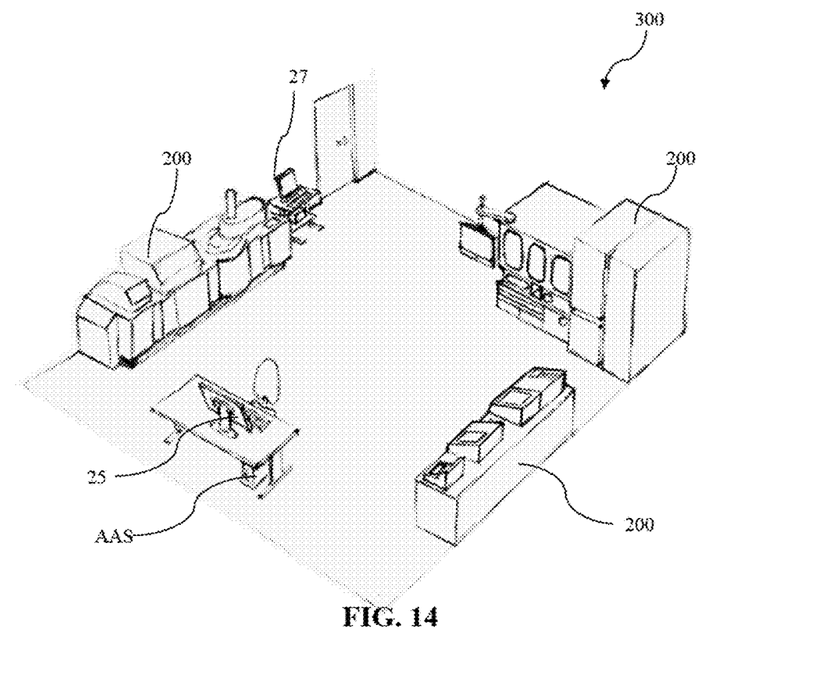
FIG. 14 illustrates a schematic diagram illustrating a laboratory system according to an embodiment of the present disclosure.

FIG. 14 shows a schematic diagram illustrating a laboratory system 300. The laboratory system 300 can comprise a plurality of laboratory devices 200 and a plurality of identification units 27, wherein any one or more of the plurality of identification units 27 can authenticate a user 100 with any one or more of the plurality of laboratory devices 200.

In order improve traceability of device usage (for regulatory or other reasons), some embodiments can further comprise the step of storing device usage data corresponding to the granting of authorization to the user 100 for the laboratory device 200. The device usage data can be retrievably accessible to a device usage monitoring unit, a functional and/or structural element of the laboratory system 300 allowing an audit trail, i.e. tracking of production relevant action(s) associated with the authenticated user 100. In some embodiments, the device usage data can be stored on the identification tag 10 by the identification unit 27.

While the present disclosure has been described in relation with laboratory devices of a laboratory system, it can be understood that the secure and convenient, identification, authentication and authorization method herein described may be employed in other fields/usage scenarios as well without departing from concept of the invention.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An identification, authentication and authorization method in a laboratory system comprising at least one laboratory device, the method comprising:
   receiving identification data from an identification tag by an identification and authentication unit, the identification data identifies a user;
   receiving identity confirmation data by the identification and authentication unit to authenticate the user;
   generating authentication data corresponding to the identification data upon successful authentication of the user, the authentication data comprising a first validity time period, wherein the authentication data is configured to enable authentication of the user based on the identification data during the first validity time period without repeated receipt of the identity confirmation data;
   receiving the identification data by an identification unit from the identification tag;
   validating the authentication data corresponding to the identification data comprising the step of verifying non-expiry of the first validity time period; and
   granting authorization to the user for the laboratory device before the expiry of the first valid time period upon successful validation of the authentication data and after re-receiving the identity confirmation data after the expiry of the first validity time period.

2. The identification, authentication and authorization method according to claim 1, wherein the identification data is provided to the identification and authentication unit by causing the identification data to be transmitted from the identification tag to an identification tag reader or by a human interface device operatively connected to the identification and authentication unit.

3. The identification, authentication and authorization method according to claim 1, further comprising,
   operatively connecting the identification and authentication unit with the identification unit to make the authentication data generated by the identification and authentication unit available to the identification unit; or storing the authentication data by the identification and authentication unit in an authentication data repository accessible by the identification unit.

4. The identification, authentication and authorization method according to claim 1, wherein the identification and authentication unit functionally and/or structurally comprises the identification unit.

5. The identification, authentication and authorization method according to claim 1, further comprising,
the identification and authentication unit encrypting and/or digitally signing the authentication data; and
the identification unit decrypting and/or verifying a digital signature of the authentication data.

6. The identification, authentication and authorization method according to claim 5, wherein the identification and authentication unit encrypts and/or digitally signs the authentication data using a preconfigured private encryption key.

7. The identification, authentication and authorization method according to claim 6, wherein the identification unit decrypts and/or verifies a digital signature of the authentication data using a preconfigured public key corresponding to the private key of the identification and authentication unit.

8. The identification, authentication and authorization method according to claim 1, further comprising,
the identification and authentication unit causes the authentication data to be stored on the identification tag, wherein the identification tag is a writable identification tag; and
after identification of the user and before validation of the authentication data, the identification unit retrieves the authentication data from the identification tag.

9. The identification, authentication and authorization method according to claim 8, wherein the identification and authentication unit causes the authentication data to be stored on the identification tag by an identification tag writer.

10. The identification, authentication and authorization method according to claim 1, further comprising,
storing the identity confirmation data within the authentication data upon successful authentication of the user by the identification and authentication unit;
providing a credential cache device functionally and/or structurally connected between a human interface device and a credential input interface operatively connected to and/or part of the laboratory device; and
authenticating the user by the credential cache device for the laboratory device by transmitting the identification data and the identity confirmation data to the credential input interface upon identifying the user with the identification unit comprised by and/or operatively to the credential cache device.

11. The identification, authentication and authorization method according to claim 10, wherein human interface device is a keyboard or keypad.

12. The identification, authentication and authorization method according to claim 10, wherein the credential cache device comprises and/or is operatively connected to the identification and authentication unit.

13. The identification, authentication and authorization method according to claim 1, wherein the laboratory system comprises a plurality of laboratory devices and a plurality of identification units, wherein any one or more of the plurality of identification units is configured to authenticate a user with any one or more of the plurality of laboratory devices.

14. The identification, authentication and authorization method according claim 1, further comprising,
storing device usage data corresponding to the granting of authorization to the user for the laboratory device, the device usage data being retrievably accessible to a device usage monitoring unit.

15. The identification, authentication and authorization method according claim 14, wherein the device usage data is stored on the identification tag by the identification unit.

16. A laboratory system, the laboratory system comprising:
at least one laboratory device;
an identification and authentication unit configured to:
receive identification data from an identification tag, the identification data identifying a user;
receive identity confirmation data to authenticate the user; and
generate authentication data corresponding to the identification data, the authentication data comprising a first validity time period upon successful authentication of the user, wherein the authentication data is configured to enable authentication of the user based on only the identification data during the first validity time period without repeated receipt of the identity confirmation data;
an identification unit configured to:
receive identification data from the identification tag;
validate the authentication data corresponding to the identification data comprising the step of verifying non-expiry of the first validity time period; and
grant authorization to the user for the laboratory device before the expiry of the first valid time period upon successful validation of the authentication data and after re-receiving the identity confirmation data after the expiry of the first validity time period.

17. The laboratory system according to claim 16, wherein the identification and authentication unit further comprises an identification tag writer configured to store the authentication data on the identification tag and wherein the identification unit is configured to retrieve the authentication data from the identification tag.

18. The laboratory system according to claim 16, wherein the identification and authentication unit is configured to store the identity confirmation data within the authentication data, the laboratory system further comprising a credential cache device functionally and/or structurally connected between a human interface device and a credential input interface operatively connected to and/or part of the laboratory device, the credential cache device being configured to authenticate the user for the laboratory device by transmitting the identification data and the identity confirmation data to the credential input interface upon identification of the user with the identification unit comprised by and/or operatively to the credential cache device.

19. The laboratory system according to claim 16, wherein the laboratory system comprises a plurality of laboratory devices and a plurality of identification units, wherein any one or more of the plurality of identification units is configured to authenticate the user with any one or more of the plurality of laboratory devices.

20. The laboratory system according to claim 16, wherein the identification and authentication unit and /or the identification unit is/are stand-alone devices of the laboratory system or functionally and/or structurally integrated into one or more laboratory device(s).

21. The laboratory system according to claim 16, wherein the identification tag is a RFID tag.

22. The laboratory system according to claim 16, wherein the identification and authentication unit is comprised within authentication and authorization system (AAS).

* * * * *